(12) United States Patent
Paternostro

(10) Patent No.: US 7,087,021 B2
(45) Date of Patent: *Aug. 8, 2006

(54) METHODS OF SCREENING FOR GENES AND AGENTS AFFECTING CARDIAC FUNCTION

(76) Inventor: Giovanni Paternostro, 517 Stratford Ct., Del Mar, CA (US) 92014

( * ) Notice: Subject to any disclaimer, the term of this patent is extended or adjusted under 35 U.S.C. 154(b) by 838 days.

This patent is subject to a terminal disclaimer.

(21) Appl. No.: 10/077,670

(22) Filed: Feb. 15, 2002

(65) Prior Publication Data

US 2002/0161302 A1  Oct. 31, 2002

Related U.S. Application Data

(60) Provisional application No. 60/270,277, filed on Feb. 20, 2001.

(51) Int. Cl.
*A61B 8/00* (2006.01)
(52) U.S. Cl. ...................................... 600/443
(58) Field of Classification Search ............... 600/437, 600/440–41, 443, 447, 454–457; 128/916
See application file for complete search history.

(56) References Cited

U.S. PATENT DOCUMENTS 4,106,438 A * 8/1978 Nelson .......................... 119/6.5

OTHER PUBLICATIONS

Adams MD, et al.. The genome sequence of *Drosophila melanogaster. Science*. 2000 ;287:2185-2195.

American Heart Association. *2000 Heart and Stroke Statistical Update*. Dallas, Tex: American Heart Association; 1999.

Artavanis-Tsakonas S, et al. Molecular cloning of Notch, a locus affecting neurogenesis in *Drosophila melanogaster. Proc Natl Acad Sci U S A* 1983; 80:1977-1981.

Ashton K, et al. Quantitative trait loci for the monoamione-related traits heart rate and headless behavior in *Drosophila melanogaster*. I.2001; 157:283-294.

(Continued)

*Primary Examiner*—Francis J. Jaworski
(74) *Attorney, Agent, or Firm*—David R. Preston & Associates A.P.C.; Raymond Wagenknecht; David Preston

(57) ABSTRACT

The relationship between aging and decreased cardiac function is well known. However, the human cardiac system is extremely complex and humans are very long-lived animals. Therefore, there is a need for simple models of the heart that can be rapidly tested over time. The fruit fly *Drosophila melanogaster* has served as a valuable model-organism for the study of aging and is the first organism possessing a circulatory system to have its genome completely sequenced. The present inventor has found that maximal heart rate is significantly and reproducibly reduced with aging in *Drosophila*, analogous to observations in elderly humans. The present inventor has also described several other aspects of the cardiac physiology of young adult and aging *Drosophila*, including an age-associated increase in rhythm disturbances. The present invention contemplates methods for studying cardiac function in vivo in adult flies. More specifically, the present invention contemplates methods of screening for genes affecting age-associated changes in cardiac function and methods of screening for agents which can affect age-associated changes in cardiac function.

33 Claims, 5 Drawing Sheets

OTHER PUBLICATIONS

Bartsch DU, et al.. Confocal scanning infrared laser ophthalmoscopy for indocyanine green angiography. *American Journal of Ophthalmology*. 1995; 120:642-651.

Bodmer R, and Venkatesh TV. Heart development in *Drosophila* and vertebrates:conservation of molecular mechanisms.*Developmental Genetics*. 1998; 22:181-186.

Burch GE, and Sohal RS, Fairbanks LD. Senescent changes in the heart of *Drosophila* repleta Wollaston. *Nature*. 1970; 225:286-288.

Burch GE, et al. Ultrastructural changes in *Drosophila* heart with age. *Archives of Pathology & Laboratory Medicine*. 1970; 89:128-136.

Curran ME, et al. A molecular basis for cardiac arrhythmia: HERG mutations cause long QT syndrome. *Cell*. 1995; 80:795-803.

Dowse H, et al. A congenital heart defect in *Drosophila* caused by an action-potential mutation. *J. Neurogenetics*, 1995; 10:153-168.

Feany MB, Bender WW. A *Drosophila* model of Parkinson's disease. *Nature*. 2000; 404:394-398.

Fleg JL, et al. Impact of age on the cardiovascular response to dynamic upright exercise in healthy men and women. *Journal of Applied Physiology*. 1995; 8:890-900.

Fortini ME, et al. A survey of human disease gene counterparts in the *Drosophila* genome. *Journal of Cell Biology*. 2000; 150:F23-F30.

Ganetzky B, and Flanagan JR. On the relationship between senescence and age-related changes in two wild-type strains of *Drosophila melanogaster*. *Exper. Gerontology*. 1978; 13:189-196.

Gang-Guo, Gu and Singh, S. Pharmacological analysis of hearbeat in *Drosophila*. *J. Neurobiol*. 1995; 28:269-280.

Johnson, E., et al. Modulation of *Drosophila* heartbeat by neurotrasmitters. 1997. *J Comp Physiol B* 167:89-97.

Johnson, E., et al. Genetic and pharmacological identification of ion channels central to the *Drosophila* cardiac pacemaker. *J. Neurogenetics*. 1998; 12:1-24.

Johnson, E., Native and heterologous neuropepticed are cardioactive in *Drosophila melanogaster*. *J. of Insect Phys*. 2000; 46:1229-1236.

Johnson, E., et al. Dynamin, encoded by *shibire*, is central to cardiac function. *J. of Expir. Zoology*. 2001; 289:81-89.

Jose AD. Effect of combined sympathetic and parasympathetic blockade on heart rate and cardiac function in man. *American Journal of Cardiology*. 1966; 18:476-478.

Kazemi-Esfarjani P, and Benzer S. Genetic suppression of polyglutamine toxicity in *Drosophila*. *Science*. 2000; 287:1837-1840.

Komuro I, and Izumo S. *Csx*: a murine homeobox-containing gene specifically expressed in the developing heart. *Proceedings of the National Academy of Sciences of the United States of America*. 1993; 90:8145-8149.

Lakatta EG. Circulatory function in younger and older humans in health. In: Hazzard WR, et al eds. *Principles of geriatric medicine and gerontology*. New York: McGraw-Hill; 1999:645-660.

Lakatta, EG. Heart aging: A fly in the ointment? *Circulation Research* 2001; 88:984-986.

Le Bourg E, Lints FA. Hypergravity and aging in *Drosophila melanogaster*. 4. Climbing activity. *Gerontology*. 1992; 38:59-64.

Lin YJ, et al. Extended life-span and stress resistance in the *Drosophila* mutant methuselah. *Science*. 1998; 282:943-946.

Lints TJ, et al. *Nkx*-2.5: a novel murine homeobox gene expressed in early heart progenitor cells and their myogenic descendants. *Development*. 1993; 119:419-431.

Min KT, and Benzer S. Preventing neurodegeneration in the *Drosophila* mutant bubblegum. *Science*. 1999; 284:1985-1988.

Nichols R., et al. Regulating the activity of a cardioacceleratory peptide, 1999. *Peptides* 20 :1153-58.

Nichols R., et al. Differential processing of neuropeptides influences *Drosophila* heart rate. *J. Neurogenetics*. 1999; 13:89-104.

Nusslein-Volhard, C., and Wiechaus, E.. Mutations affecting segment number and polarity in *Drosophila*. *Nature*. 1980; 287:795-801.

Ohno S. Ancient linkage groups and frozen accidents. *Nature*. 1973; 244:259-262.

Paternostro G, et al. Age-associated cardiac dysfunction in *Drosophila melanogaster*, *Circulation Research*, 2001; 88:1053-1058.

Pennisi E. Evolutionary trends from bacteria to birds. *Science*. 2000; 289:1131-1133.

Rich MW. Heart failure. In: Hazzard WR, et al, eds. *Principles of geriatric medicine and gerontology*. New York: McGraw-Hill; 1999:679-700.

Roberts J, and Goldberg PB. Changes in basic cardiovascular activities during the lifetime of the rat. *Experimental Aging Research*. 1976; 2:487-517.

Robins J, et al. Genetic variation affecting heart rate in *Drosophila melanogaster*. *Genet. Res., Camb*. 1999; 74:121-128.

Sinclair DA, et al. Molecular mechanisms of yeast aging. *Trends in Biochemical Sciences*. 1998;23:131-134.

Tower J. Aging mechanisms in fruit flies. *BioEssays*. 1996; 18:799-807.

Yu BP, et al.. Life span study of SPF Fischer 344 male rats fed *ad libitum* or restricted diets: longevity, growth, lean body mass and disease. *Journal of Gerontology*. 1982;37:130-141.

White, K., et al. Genetic control of programmed cell death in *Drosophila*. *Science* 1999; 264:677-683.

Warmke JW, Ganetzky B. A family of potassium channel genes related to *eag* in *Drosophila* and mammals. *Proc Natl Acad Sci U S A*. 1994;91:3438-3442.

White, L..Aet al. Effects of deuterium oxide and temperature on heart rate in *Drosophila melanogaster* 1992. *J Comp Physiol B* 162:278-83.

Zomik, E, et al. Neuraltransmitters and a peptide modulate *Drosophila* heart rate. *Peptides*, 1999;20:45-51.

St. Johnston, D. The art and design of genetic screens: *Drosophila melanogaster*. *Nature*. 2002; 3:176-188.

Rizki TM. The Circulatory System and Associated Cells and Tissues. In: Ashburner M, Wright TRF, Eds. *The Genetics and Biology of Drosophila*. London: Academic Press; 1978:397-452.

\* cited by examiner

METHODS OF SCREENING FOR GENES AND AGENTS AFFECTING CARDIAC FUNCTION This application claims benefit of co-pending Provisional U.S. Patent Application Ser. No. 60/270,277 filed Feb. 20, 2001, entitled "Screening procedure for genes or agents affecting the heart," incorporated herein by reference.

TECHNICAL FIELD

The present invention relates generally to the field cardiology and more particularly to methods of identifying genes and compounds involved in heart function including age-related changes in heart function.

BACKGROUND

The relationship between aging and heart disease is well known (American Heart Association. 2000 *Heart and Stroke Statistical Update*. Dallas, Tex.: American Heart Association; 1999). The prevalence of heart failure is almost 70 times higher in persons 65 years of age or older, compared to persons aged 20–34 years (American Heart Association. 2000 *Heart and Stroke Statistical Update*. Dallas, Tex. American Heart Association; 1999). Furthermore, cardiac functional reserve declines with age in humans (Fleg J L, et al. Impact of age on the cardiovascular response to dynamic upright exercise in healthy men and women. *Journal of Applied Physiology*. 1995;78:890–900; Lakatta E G. Circulatory function in younger and older humans in health. In: Hazzard W R, Blass J P, Ettinger W H, Halter J B, Ouslander J G, eds. *Principles of geriatric medicine and gerontology*. New York: McGraw-Hill; 1999:645–660). Nearly 80% of hospital admissions in the United States for heart failure involve patients over 65 years of age (Rich M W. Heart failure. In: Hazzard W R, Blass J P, Ettinger W H, Halter J B, Ouslander J G, eds. *Principles of geriatric medicine and gerontology*. New York: McGraw-Hill; 1999:679–700). Due to the complexity of the human organism and its long life-span, there is a need for simple model systems for identifying genes and agents involved in cardiac function, including changes in cardiac function that are related to aging. A need exists for appropriate models for studying the aging of tissues that have very limited replicative capacity, such as the heart, which play an important role in determining human mortality.

The genome of *Drosophila melanogaster* was the first to be fully sequenced for an animal possessing a circulatory system (Adams M D, et al., The genome sequence of *Drosophila melanogaster*. *Science*. 2000;287:2185–2195). The heart of the fly consists of a tubular structure that contracts spontaneously throughout the insect lifespan and has the main function of circulating the hemolymph, which transports energy substrates from the abdomen to the thorax and head (Rizki T M. The Circulatory System and Associated Cells and Tissues. In: Ashburner M, Wright T R F, Eds. *The Genetics and Biology of Drosophila*. London: Academic Press; 1978:397–452). Investigating age-associated changes in *Drosophila* with a focus on cardiac function has clear advantages. By directly assessing the status of the heart, the complexity of the object of study is reduced, which should yield a smaller, more manageable, set of candidate genes for subsequent analysis after initial genetic screens. Furthermore, several of the most promising models used in aging research (yeast (Sinclair D A, Mills K, Guarente L. Molecular mechanisms of yeast aging. *Trends in Biochemical Sciences*. 1998;23:131–134) and recently even bacteria (Pennisi E. Evolutionary trends from bacteria to birds. *Science*. 2000;289:1131–1133)) are only informative for the replicative senescence of actively dividing cells.

Many important findings for human medicine and biology have originated from studies in *Drosophila*. Examples are the identification of genes regulating embryonic development (Nusslein-Volhard C. and Wieschaus E. 1980. Mutations affecting segment number and polarity in *Drosophila*. *Nature* 287:795–801), the initial identification of several components of the apoptotic machinery (White K. et al. 1994. Genetic control of programmed cell death in *Drosophila*. *Science* 264:677–683), and elucidation of gene pathways involved in neurogenesis (Artavanis-Tsakonas S. et al. 1983. Molecular cloning of Notch, a locus affecting neurogenesis in *Drosophila melanogaster*. *Proc Natl Acad Sci USA* 80:1977–1981).

Several groups have exploited *Drosophila* genetics for identifying genes regulating cardiac development in the fly, and this approach has been useful for guiding research on cardiac development in vertebrates. For example, Bodmer and Venkatesh (Heart development in *Drosophila* and vertebrates: conservation of molecular mechanisms. *Developmental Genetics*. 1998;22:181–186) reported the identification of the *Drosophila* gene tinman, which prompted the cloning of homologues regulating cardiac development in mice (Nkx2-5/Csx) by Lints et al. (Lints T J, et al. Nkx-2.5: a novel murine homeobox gene expressed in early heart progenitor cells and their myogenic descendants. *Development*. 1993; 119:419–4) and Komuro et al. (Komuro I, Izumo S. Csx: a murine homeobox-containing gene specifically expressed in the developing heart. *Proceedings of the National Academy of Sciences of the United States of America*. 1993;90:8145–8149). The finding of homologous genes that similarly influence development of the heart-like organ of *Drosophila* and the mouse heart indicates that some aspects of fly cardiac biology are common to mammals. The relevance of some fly genes to human cardiac pathology is supported by the finding, by Curran et al. (Curran M E, et al. A molecular basis for cardiac arrhythmia: HERG mutations cause long QT syndrome. *Cell*. 1995;80:795–803), that mutations in the HERG potassium channel gene cause long-QT syndrome, a potentially fatal cardiac arrhythmia (Curran M E, et al., A molecular basis for cardiac arrhythmia: HERG mutations cause long QT syndrome. *Cell*. 1995;80:795–803). HERG was first identified by virtue of its homology to the *Drosophila* potassium channel gene "ether-a-go-go" (Warmke J W, Ganetzky B. A family of potassium channel genes related to eag in *Drosophila* and mammals. *Proc Natl Acad Sci USA*. 1994;91:3438–3442).

Several human disease models have been developed in *Drosophila*, particularly for neurological diseases (Min K T, Benzer S. Preventing neurodegeneration in the *Drosophila* mutant bubblegum. *Science*. 1999;284:1985–1988; Kazemi-Esfarjani P, Benzer S. Genetic suppression of polyglutamine toxicity in *Drosophila*. *Science*. 2000;287:1837–1840; Feany M B, Bender W W. A *Drosophila* model of Parkinson's disease. *Nature*. 2000;404:394–398). *Drosophila* is also commonly employed as a model-organism for studying the genetics of aging, partly because it represents a genetically tractable organism with a short life span (Rose M R. *Evolutionary Biology of Aging*. New York: Oxford University Press; 1991). For example, a gene that controls life span in flies was identified by genetic screens (Lin Y J, Seroude L, Benzer S. Extended life-span and stress resistance in the *Drosophila* mutant methuselah. *Science*. 1998;282:943–946). The search for genes extending life span in *Drosophila* is actively underway and has recently begun to provide insights into the genetics of aging in this animal (Lin Y J, Seroude L, Benzer S. Extended life-span and stress resistance in the *Drosophila* mutant methuselah. *Science.* 1998;282:943–946). Mutant flies have been screened for variations in life-span, revealing that single gene mutations can increase the life-span by as much as 35% in these invertebrate animals. The problem with these methods is two-fold. First, the predominant causes of death in aged fruit flies are unknown and might be largely irrelevant to those affecting humans. Second, in rats the main causes of mortality in old animals (kidney disease and certain types of cancer) are not the same illnesses that are the most common causes of death in humans (Yu B P, et al. Life span study of S P F Fischer 344 male rats fed ad libitum or restricted diets: longevity, growth, lean body mass and disease. *Journal of Gerontology.* 1982;37:130–141).

Therefore fly screens based on mortality could lead to the identification of genes affecting a physiological process, maybe irrelevant to human health.

Other groups have examined fly cardiology at the cellular level. A few manuscripts from the early seventies report abnormalities in cardiac cell ultrastructure (especially involving mitochondria) in the hearts of aged flies, as studied by electron microscopy (Burch G E, Sohal R S, Fairbanks L D. Senescent changes in the heart of *Drosophila repleta* Wollaston. *Nature.* 1970;225:286–288; Burch G E, et al. Ultrastructural changes in *Drosophila* heart with age. *Archives of Pathology & Laboratory Medicine.* 1970;89: 128–136). However, functional assessments of the whole heart have not been performed. Essentially nothing is known about cardiac changes that might occur with aging in the fly and attempts have not been made to exploit *Drosophila* genetics for investigations of adult cardiac dysfunction.

A commonly recognized limitation in the search for single gene mutations that can lengthen the lifespan of *Drosophila* is inbreeding depression (Tower J. Aging mechanisms in fruit flies. *BioEssays.* 1996;18:799–807). To make a recessive mutation homozygous and to analyze its phenotype in *Drosophila* requires inbreeding and this favors the fixation of alleles possessing a deleterious effect on lifespan. Working on a parameter that can be measured throughout life (heart function) should allow us to identify beneficial mutations, detecting their effect at early ages, even against an unfavorable genetic background due to inbreeding that could shorten the lifespan non-specifically.

Another advantage of using the fly as a model pertains to the size of its genome. Whereas the human genome may contain over 60,000 genes, only approximately 14,000 genes have been identified in the fly genome (Adams M D, et al. The genome sequence of *Drosophila melanogaster. Science.* 2000;287:2185–2195). According to Ohno's widely accepted hypothesis, two rounds of gene duplications are believed to have occurred in the human genome since the last common ancestor shared with *Drosophila* (Ohno S. Ancient linkage groups and frozen accidents. *Nature.* 1973; 244:259–262). Human genes are often members of extended families with redundant functions, making genetic analysis problematic in higher eukaryotes compared to invertebrates such as *C. elegans* or *Drosophila*. Thus, approaching the problem of age-associated cardiac deterioration in a genetically tractable organism such as the fly can help to avoid genetic redundancy.

Other methods of studying the function of the fly heart are not satisfactory when compared with the present invention. For example, the method of White et al. (Effects of deuterium oxide and temperature on heart rate in *Drosophila melanogaster* 1992. *J Comp Physiol B* 162:278–83) and Johnson et al. (Modulation of *Drosophila* heartbeat by neurotransmitters. 1997. *J Comp Physiol B* 167:89–97) is limited to early pupae or larvae, not adults, and only heart rate can be measured, images are not obtained. Heart rate is not a very good measure of cardiac work if other parameters, e.g. fractional shortening, are not obtained. Using their method the animals are immersed in a drop of water and the results are therefore not physiological because respiration is impaired. The method of Nichols et al. (Regulating the activity of a cardioaccelleratory peptide. 1999. *Peptides* 20:1153–58) also has the limitations of measuring only heart rate and of the use of water drop immersion. With these authors' methods, images are not obtained. More importantly, with these author's methods, only relative changes from a baseline during an acute (less than 10 minutes) experiment can be reliably measured and absolute data from individuals cannot be compared, therefore these methods are not suitable for studying age-related or genetic changes.

The present inventor found that genetic screens based on age-associated differences in heart rates under the stress of elevated temperature can be exploited for identifying evolutionarily conserved genes that either accelerate or retard the rate of age-associated cardiac decline in *Drosophila*. Given that a recent survey has shown remarkable conservation of human genes in the fly genome, including cardiac disease-relevant genes (Fortini M E, et al. A survey of human disease gene counterparts in the *Drosophila* genome. *Journal of Cell Biology.* 2000;150:F23–F30), candidate genes identified by such genetics screens have a strong possibility of being relevant to humans.

Therefore, there is a need to determine if an age-associated decline in some aspect of cardiac performance occurs. There is a need to develop a methodology for studying the heart-like organ in intact adults. In addition, there is a need to develop methods that can quickly measure fly heart function, so that rapid screening of genes or compounds can be made. It is the object of the present invention to address these unresolved needs.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific aspects presented herein.

was measured in young (10 days of age) and old (54 days) flies using the Diaphot microscope, at different temperatures (22° C. (n=59,64), 28° C. (n=10,7), 32° C. (n=10,9), 35° C. (n=10,9) and 38° C. (n=5,5)). A plateau was reached at approximately 35° C. Data are mean±standard error of the mean.

Figure 4:
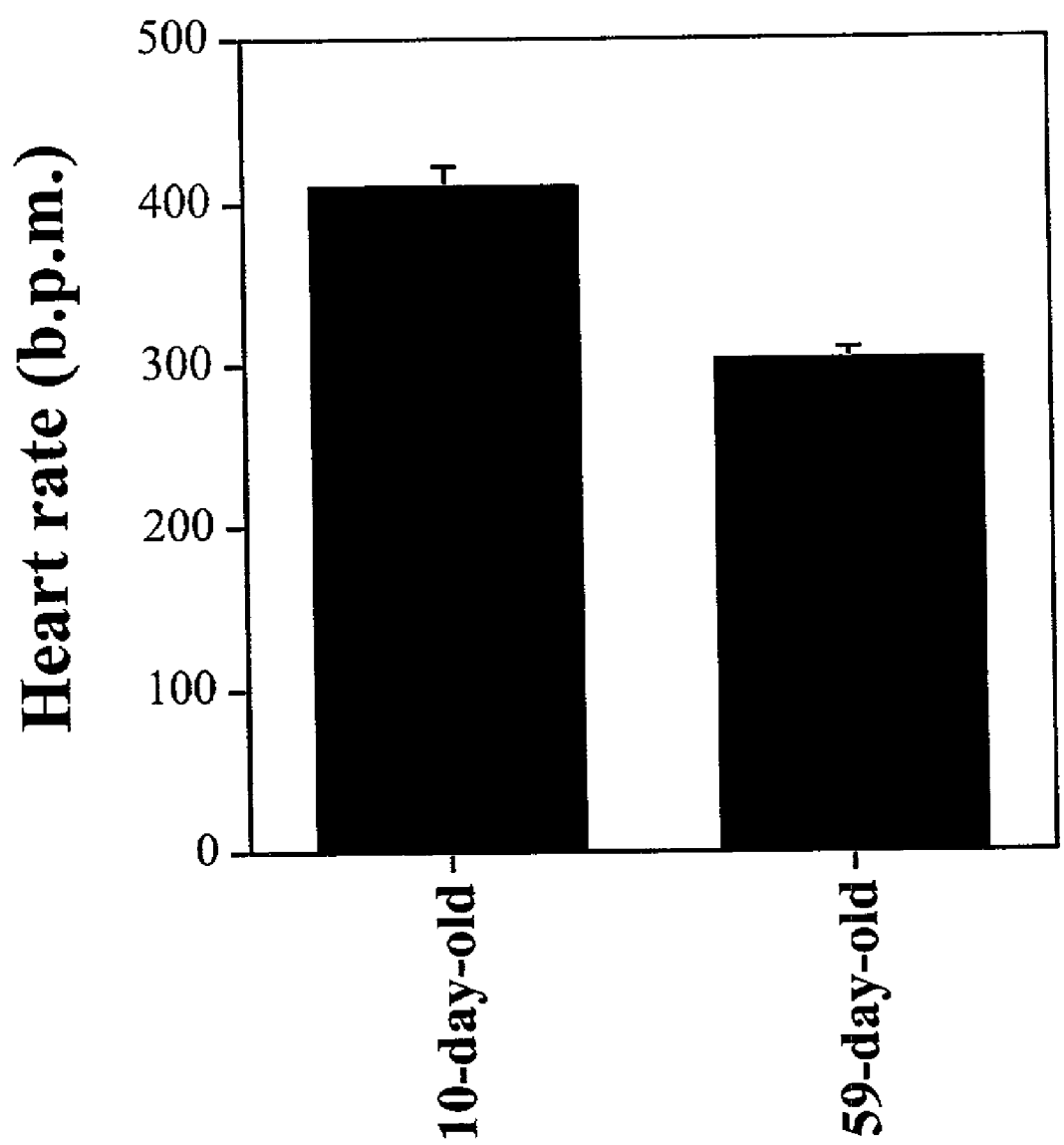

FIG. 4 depicts maximal heart rate during electrical pacing in young and old flies. Heart rate (in beats per minute) was measured in young (10 days of age) and old (59 days) flies during the electrical pacing protocol. Data are mean ± standard error of the mean (n=15,14).

Figure 5:
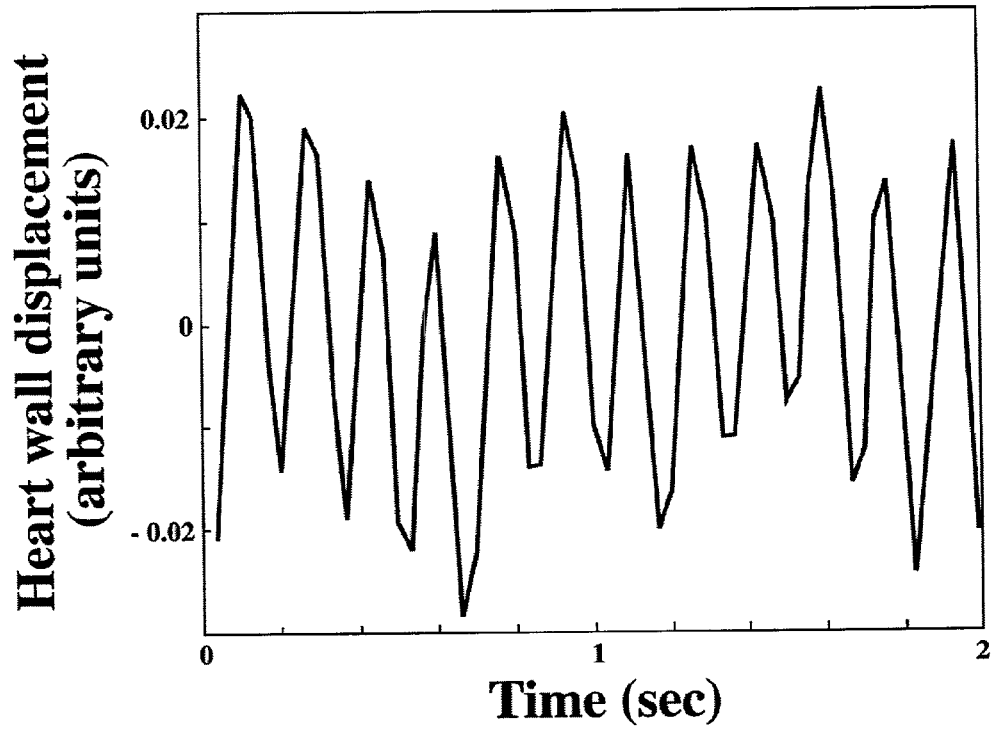
Figure 5:
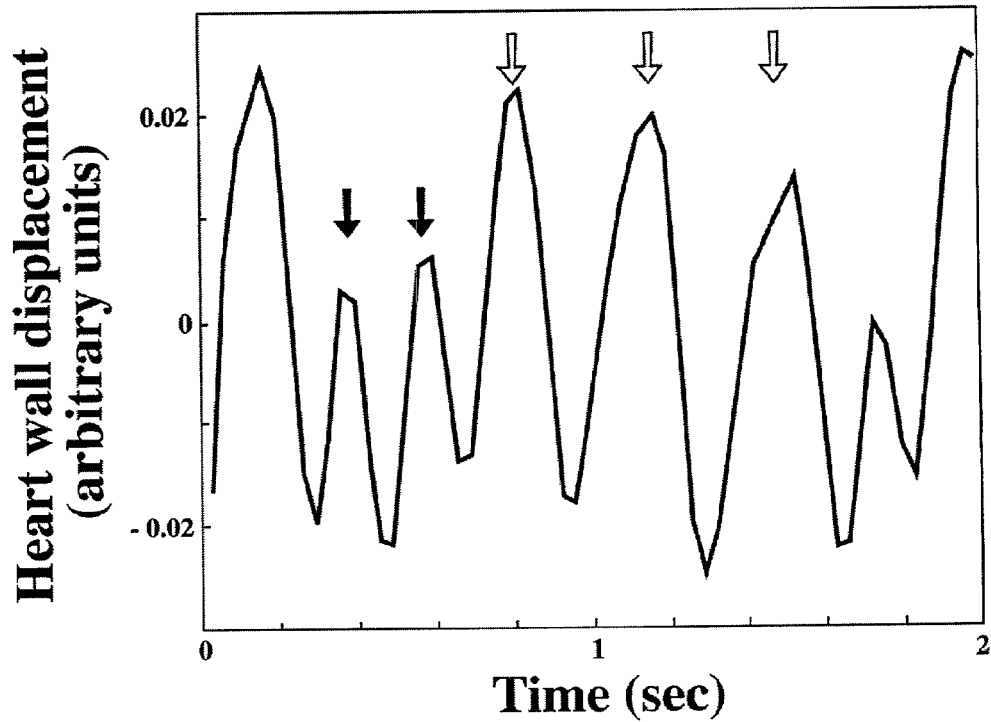

FIG. 5 depicts heart wall displacement plots obtained with the automated heart rate detection software. Heart wall displacement plots obtained in a young (6-day-old, UPPER PANEL) and aged (47-day-old, LOWER PANEL) fly. Software was used to estimate the heart rate and the variability with time. The aged fly plot displays a lower number of beats and increased variability in the intervals between beats (compare black and white arrows).

SUMMARY OF THE INVENTION

The present invention recognizes that new methods are needed for screening for genes and compounds involved in impairments and enhancements of cardiac function, said impairments being commonly revealed only under stress, since resting function is affected only in very advanced forms of cardiac disease (Fleg J L, et al. Impact of age on the cardiovascular response to dynamic upright exercise in healthy men and women. *Journal of Applied Physiology.* 1995;78:890–900; Lakatta E G. Circulatory function in younger and older humans in health. In: Hazzard W R, Blass J P, Ettinger W H, Halter J B, Ouslander J G, eds. *Principles of geriatric medicine and gerontology*. New York: McGraw-Hill; 1999:645–660). The present invention lays a foundation for genome-wide screens for genes that accelerate or retard age-associated heart disease using *Drosophila*. The present invention provides materials and methods for identifying genes that affect cardiac function, using *Drosophila* as a model system. The present invention also provides materials and methods for identifying agents important in age-related changes of cardiac function, using *Drosophila* as a model system. As a non-limiting introduction to the breath of the present invention, the present invention includes several general and useful aspects, including:

One aspect of the present invention is a method (referred to as Method 1) of screening for a gene affecting the cardiac function including the steps of providing a *Drosophila*, imaging the heart of the *Drosophila*, measuring the movements of the heart in the image, and analyzing the measurements of the heart movements; whereby the effect of the gene on cardiac function is determined. In one preferred aspect of the present invention, the heart of the *Drosophila* is electrically paced with electrodes and a pulse generator, so that parameters selected from the group consisting of the maximal heart rate and the frequency of occurrence of fibrillation-like rhythm are determined. In another preferred aspect of the present invention, the temperature is increased to stress the heart. In yet another preferred aspect of the present invention the effect of said gene on age-related changes in cardiac function is determined.

A second aspect of the present invention is a method (referred to as Method 2) of screening for agents affecting cardiac function including the steps of providing a *Drosophila*, exposing the *Drosophila* to a test agent, imaging the heart of the *Drosophila*, measuring the movements of the heart in the image, and analyzing the measurements of the movements; whereby the analysis of the measurements are indicative of the cardiac function of said *Drosophila* and changes in the function are indicative of the effect of the test agent on the cardiac function of the *Drosophila*. Another preferred aspect of the present invention includes the step of electrically pacing the heart with electrodes and a pulse generator, so that parameters selected from the group consisting of the maximal heart rate and the frequency of occurrence of fibrillation-like rhythm are determined. Yet another preferred aspect of the present invention includes the step of increasing the temperature to stress the heart. Still more preferred, the effect of the test agent on age-related changes in cardiac function is determined.

DETAILED DESCRIPTION OF THE PREFERRED ASPECTS

The present invention is based in part on the present inventor's discovery of an age-associated reduction in heart rate in flies, which is consistent with the decrease in exercise capacity observed in *Drosophila* with aging (Le Bourg E, Lints F A. Hypergravity and aging in *Drosophila melanogaster*. 4. Climbing activity. *Gerontology.* 1992;38:59–64; Ganetzky B, Flanagan J R. On the relationship between senescence and age-related changes in two wild-type strains of *Drosophila melanogaster. Experimental Gerontology.* 1978;13:189–196). In this regard, it has been documented that aging flies have reduced exercise tolerance compared to young flies, as measured by climbing ability. The inventor's observations thus reveal intriguing similarities between the decline in cardiac function during aging in flies and humans. Data from the Baltimore Longitudinal Study of Aging, for example, demonstrated that a significant but limited reduction of resting heart rate occurs with age in humans. However, Fleg et al. also documented that a much more pronounced decrease in maximum heart rate achieved during exercise is associated with aging (Fleg J L, et al. Impact of age on the cardiovascular response to dynamic upright exercise in healthy men and women. *Journal of Applied Physiology.* 1995;78:890–900). The intrinsic sinus rate in humans (measured in the presence of both sympathetic and parasympathetic blockade) is also significantly diminished with age (Jose A D. Effect of combined sympathetic and parasympathetic blockade on heart rate and cardiac function in man. *American Journal of Cardiology.* 1966;18:476–478). Age-related changes in heart rate have also been reported in rats (Roberts J, Goldberg P B. Changes in basic cardiovascular activities during the lifetime of the rat. *Experimental Aging Research.* 1976;2:487–517).

DEFINITIONS

Following long standing patent law convention, the singular forms "a," "an," and "the" include plural references in this specification, including the claims, unless the content clearly dictates otherwise.

Unless defined otherwise, all technical and scientific terms used herein have the same meaning as commonly understood by one of ordinary skill in the art to which this invention belongs. Generally, the nomenclature used herein and the laboratory procedures in cardiology, microscopy, chemistry, genetics, biology, molecular biology, cell science and cell culture described below are well known and commonly employed in the art. Conventional methods are used for these procedures, such as those provided in the art and various general references such as, *Heart Disease* (Braunwald E, 2001), *Drosophila. A Laboratory Handbook* (Ashbumer M, 1989); *Drosophila* (Roberts D B, 1998); *Light Microscopy in Biology* (Lacey A J, 1999); *Video Microscopy: The Fundamentals* (Inoue S and Spring K R, 1997) and *Image Processing and Analysis* (Baldock R and Graham J, 2000). Where a term is provided in the singular, the inventor also contemplates the plural of that term. Other technical terms used herein have their ordinary meaning in the art that they are used, as exemplified by a variety of technical dictionaries.

The term "gene" is known to those of ordinary skill in the art. In the context of the present invention, "gene" is understood to include the coding region and optionally regulatory elements, such as up-stream and down-stream regulatory elements, including promoter elements, and cis and trans elements. The "gene" may or may not contain a mutation, which may or may not alter expression of such gene.

INTRODUCTION

As a non-limiting introduction to the breadth of the present invention, the present invention includes several general and useful aspects, including:

1) Methods of screening for genes involved in cardiac function, especially genes involved in age-related changes in cardiac function (referred to herein as Method 1).

2) Methods of screening for agents affecting cardiac function, especially agents affecting age-related changes in cardiac function (referred to herein as Method 2).

I. Method 1: Methods of Screening for Genes Involved in Cardiac Function

The present invention provides materials and methods for identifying genes that affect cardiac function, including age-related changes of cardiac function, using *Drosophila* as a model system. The present invention also provides materials and methods for identifying agents that affect cardiac function, including age-related changes of cardiac function, using *Drosophila* as a model system. As a non-limiting introduction to the breadth of the present invention, the present invention includes several general and useful aspects, including:

One aspect of the present invention is a method of screening for genes affecting cardiac function comprising the steps of providing an adult *Drosophila*, imaging the heart of the *Drosophila*, measuring the movements of the heart in the image, and analyzing the measurements of the heart movements; whereby the analysis of the measurements are indicative of the cardiac function of the *Drosophila* and changes in the function of the heart are indicative of the effect of the gene on the cardiac function of the *Drosophila*. Preferably the effects of said gene, on age-related changes in said cardiac function, is determined. Preferably, the movements of the heart walls are measured, including heart function; and the measurements are analyzed, whereby the results of the analysis are indicative of the effect of a gene on the cardiac function of the *Drosophila*. In preferred aspects of the present invention, control flies are examined, their heart movements are measured and the data analyzed, and the results of the analysis are compared to the results of analyzed data from test flies, whereby the results of the analysis and comparison of results are indicative of the effect of a gene on the cardiac function of the *Drosophila*.

In preferred aspects of the present invention, the *Drosophila* is positioning under a microscope so that the light beam of the microscope is both generally perpendicular to the frontal plane of the *Drosophila* and is generally directed on the heart of the *Drosophila*. In further preferred aspects of the present invention, contrast enhancement means, such as Nomarski (DIC) optics or adjusting the field diaphragm and the condenser iris diaphragm, are combined with the microscope to enhance the image of the *Drosophila* heart.

In preferred aspects of the present invention, the method includes the step of electrically pacing the *Drosophila's* heart with electrodes and a pulse generator, so that maximal heart rate and the frequency of occurrence of fibrillation-like rhythm are determined. More preferably, platinum electrodes and a Model 611 square wave stimulator (a pulse generator from Phipps & Bird, Richmond, Va.) are used for external cardiac pacing. The electrodes are positioned on the ventral surface of the abdomen of the fly using a micromanipulator, while heart images are recorded. Electrode gel (electrolyte gel, preferably Signa gel, Parker, Fairfield, N.J.) is applied to the electrodes. Sill more preferably the pacing protocol consisted of pulses of about 20 seconds duration, with each pulse followed by a recovery period of about 1 minute. The pacing rate is increased in 1 Hz steps for each fly from about 5 Hz (300 beats per minute) to about 8 Hz (480 beats per minute). The duration of the pacing stimuli is about 30 milliseconds and the voltage is 30 about 40 volts. Lower voltages and durations failed to capture consistently during external pacing.

Further preferred aspects of the present invention include the step of increasing the temperature to stress the *Drosophila's* heart. For example, the temperature is increased progressively from about 22° C. to about 28° C. over a course of time, probably between about 15 minutes to two hours, more preferably about one hour. Measurements are taken at from about 22° C. to about 28° C. A control group is kept at room temperature for the same amount of time under about the same conditions of immobilization, and does not show a significant change in heart rate. In another example, the anesthetized flies are inserted into an incubator containing the Diaphot microscope approximately 2 minutes before recording. This is done in separate groups at the temperatures from about 28° C. to about 38° C.

A further aspect of the present invention is the alteration of the gene is a mutation. In an additional aspect of the present aspect, the mutation of the gene results in a change, increase or decrease, in said gene's expression. The change in expression can be caused by a mutation in the gene, such as in a regulatory element, or a change in cellular signaling that regulates expression of the gene. In yet further aspects of the present invention, the effect of the gene on age-related changes in the *Drosophila's* cardiac function is determined.

In preferred aspects of the present invention, said *Drosophila* is a *Drosophila melanogaster*. Another preferred aspect is transgenic *Drosophila melanogaster* expressing a fluorescent marker in the heart, such as Green Fluorescence Protein or luceferase under the control of an appropriate promoter, such as, for example, an actin-promoter. Still more preferred, the flies are maintained at about 24° C. in continuous light and about 50% relative humidity in bottles, with about 40 flies per bottle. The flies are fed a standard yeast-cornmeal-molasses-agar diet and transferred to new bottles every few days, as is commonly done in the art.

In further preferred aspects of present invention, the anesthesia of the *Drosophila* is caused by an approximately 50% solution triethylamine, preferably Flynap™ (Carolina Biological Supply Company, NC). More preferably, the triethylamine is administered by dipping an absorbent wand into the anesthetic and then inserting the anesthetic-containing wand into the vial containing the flies. The flies are removed from the vial as soon as they are immobile.

In yet another preferred aspect of the present invention, the microscope is a fluorescence microscope. A more preferred aspect the microscope is a Nikon Diaphot-TMD inverted microscope, with Nomarski (DIC) optics (without analyzer) and a 10×(N.A. 0.25) objective. Preferably, images are obtained by closing the field diaphragm, so that the light-beam is concentrated on the first ventricle of the fly's heart, and the intensity of the light-beam is increased to the maximum. Most preferably, the flies are positioned on their backs, approximately perpendicular to the light path, and fixed in this position by mounting the spread wings on a glass slide with double-stick tape. Images of the first cardiac ventricle are recorded using a Sony DXC-101 video camera on VHS tape, or using a similar recording apparatus, and the heart rate is measured from slow-motion replays. End-diastolic and end-systolic dimensions are measured on still images at the mid-point between the two major transversal tracheal tubes passing over the first cardiac ventricle. The images can also be analyzed by appropriate image analysis software. In certain aspects of the present invention semi-automated digital image processing is used to measure heart rate and its variation directly from video signals recorded in a single fly or multiple flies. Automated detection allows parameters such as heart rate variability to be detected in a single fly. In preferred aspects of the present invention, video image sequences are acquired to the memory of a Pentium II based microcomputer using a high-resolution video frame grabber, such as Data Translation DT3155, at a sampling frequency of 30 frames per second. For each fly 2-second video sequences (60 frames each) 10 times consecutively are acquired. In more preferred aspects of the present invention, software is used to construct a time-space image signal representing the time course of image intensity along a line segment of pixels that crosses the ventricular lumen transverse to the heart axis. After applying a low pass filter to reduce noise in the time-space signal, heart rate is estimated by automated counting of the peaks in the signal. From the unfiltered time-space signal a second measure of heart rate is obtained by computing the autocorrelation and then the spectral density (using a Fast Fourier Transformation, Chatfield C. *The Analysis of Time Series.* London: Chapman and Hall; 1980) confirming the previous calculation. An average and a standard deviation of the repetitions in the same fly, for example (i.e. about 10 repetitions) are obtained and the coefficient of variation is calculated (Armitage P, Berry G. *Statistical Methods in Medical Research.* 3rd ed. Oxford: Blackwell Scientific; 1994).

The present invention discloses a gene identified by Method 1.

II. Method 2: Methods of Screening for Agents Affecting Cardiac Function

One aspect of the present invention is a method of screening for agents affecting cardiac function comprising the steps of providing an adult *Drosophila,* exposing the *Drosophila* to one or more test agents; imaging the heart of the *Drosophila,* measuring the movements of the heart in the image, and analyzing the measurements of the heart movements; whereby the analysis of the measurements are indicative of the cardiac function of the *Drosophila* and changes in the function of the heart are indicative of the effect of the test agent on the cardiac function of the *Drosophila.* The *Drosophila* may be exposed the test agent for various lengths of time, ranging from several days to about a minute. The *Drosophila* may be exposed to the test agent in various ways, including microinjection, eating, breathing, and absorbing through the endoskeleton. Preferably the effects of the agent, on age-related changes in said cardiac function, is determined. Preferably, the movements of the heart walls are measured, including heart function; and the measurements are analyzed, whereby the results of the analysis are indicative of the effect of the agent on the cardiac function of the *Drosophila.*

In preferred aspects of the present invention, the *Drosophila* is positioning under a microscope so that the light beam of the microscope is both generally perpendicular to the frontal plane of the *Drosophila* and is generally directed on the heart of the *Drosophila.* In further preferred aspects of the present invention, contrast enhancement means, such as Nomarski (DIC) optics or adjusting the field diaphragm and the condenser iris diaphragm, are combined with the microscope to enhance the image of the *Drosophila* heart.

In preferred aspects of the present invention, the method includes the step of electrically pacing the *Drosophila's* heart with electrodes and a pulse generator, so that maximal heart rate and the frequency of occurrence of fibrillation-like rhythm are determined. More preferably, platinum electrodes and a Model 611 square wave stimulator (a pulse generator from Phipps & Bird, Richmond, Va.) are used for external cardiac pacing. The electrodes are positioned on the ventral surface of the abdomen of the fly using a micromanipulator, while heart images are recorded. Electrode gel (electrolyte gel, preferably Signa gel, Parker, Fairfield, N.J.) is applied to the electrodes. Sill more preferably the pacing protocol consisted of pulses of about 20 seconds duration, with each pulse followed by a recovery period of about 1 minute. The pacing rate is increased in 1 Hz steps for each fly from about 5 Hz (300 beats per minute) to about 8 Hz (480 beats per minute). The duration of the pacing stimuli is about 30 milliseconds and the voltage is about 40 volts. Lower voltages and durations failed to capture consistently during external pacing.

Further preferred aspects of the present invention include the step of increasing the temperature to stress the *Drosophila's* heart. For example, the temperature is increased progressively from about 22° C. to about 28° C. over a course of time, probably between about 15 minutes to two hours, more preferably about one hour. Measurements are taken at from about 22° C. to about 28° C. A control group is kept at an appropriate temperature, such as 25° C., for about the same amount of time under about the same conditions of immobilization, and does not show significant changes in heart rate. In another example, the anesthetized flies are inserted into an incubator containing the Diaphot microscope for an appropriate abount of time, such as approximately 2 minutes, before recording. This is done in separate groups at the temperatures from about 28° C. to about 38° C.

In preferred aspects of the present invention, said *Drosophila* is a *Drosophila melanogaster.* Another preferred aspect is transgenic *Drosophila melanogaster* expressing a fluorescent marker in the heart, such as Green Fluorescence Protein or luciferase under the control of an appropriate promoter, such as the actin-promoter. Still more preferred, the flies are maintained at about 24° C. in continuous light and about 50% relative humidity in bottles, with about 40 flies per bottle. The flies are fed a standard yeast-cornmeal-molasses-agar diet and transferred to new bottles every few days, as is commonly done in the art.

In further preferred aspects of present invention, the anesthesia of the *Drosophila* is caused by an approximately 50% solution triethylamine, preferably Flynap™ (Carolina Biological Supply Company, NC). More preferably, the triethylamine is administered by dipping an absorbent wand into the anesthetic and then inserting the anesthetic-containing wand into the vial containing the flies. The flies are removed from the vial as soon as they are immobile.

In yet another preferred aspect of the present invention, the microscope is a fluorescence microscope. A more preferred aspect the microscope is a Nikon Diaphot-TMD inverted microscope, with Nomarski (DIC) optics (without analyzer) and a 10× (N.A. 0.25) objective. Preferably, images are obtained by closing the diaphragm, so that the light-beam is concentrated on the first ventricle of the fly's heart and the intensity of the light-beam is increased to the maximum. Most preferably, the flies are positioned on their backs, approximately perpendicular to the light path, and fixed in this position by mounting the wings on a glass slide with double-stick tape. Images of the first cardiac ventricle are recorded using a Sony DXC-101 video camera on VHS tape, or using a similar recording apparatus, and the heart rate is measured from slow-motion replays. End-diastolic and end-systolic dimensions are measured on still images at the mid-point between the two major transversal tracheal tubes passing over the first cardiac ventricle. The images can also be analyzed by image analysis software. In certain aspects of the present invention semi-automated digital image processing is used to measure heart rate and its variation directly from video signals recorded in a single fly or multiple flies. Automated detection allows parameters such as heart rate variability to be detected in a single fly. In preferred aspects of the present invention, video image sequences are acquired to the memory of a Pentium II based microcomputer using a high-resolution video frame grabber, such as Data Translation DT3155, at an appropriate sampling frequency, such as about 30 frames per second. For each fly about 2-second video sequences (60 frames each) about 10 times consecutively are acquired. In more preferred aspects of the present invention, software is used to construct a time-space image signal representing the time course of image intensity along a line segment of pixels that crosses the ventricular lumen transverse to the heart axis. After applying a low pass filter to reduce noise in the time-space signal, heart rate is estimated by automated counting of the peaks in the signal. From the unfiltered time-space signal a second measure of heart rate is obtained by computing the autocorrelation and then the spectral density (using a Fast Fourier Transformation, Chatfield C. *The Analysis of Time Series*. London: Chapman and Hall; 1980) confirming the previous calculation. An average and a standard deviation of an appropriate number of repetitions, such as about 10 repetitions, in the same fly, or different or multiple flies, are obtained and the coefficient of variation is calculated (Armitage P, Berry G. *Statistical Methods in Medical Research*. 3rd ed. Oxford: Blackwell Scientific; 1994).

In preferred aspects of the present invention, the data from flies exposed to the test agent is compared to data from control flies, such as wild type flies, of the same age and culture conditions as the test fly, that have never been exposed to any agents.

The present invention discloses an agent identified by Method 2.

EXAMPLES

Example 1

Transgenic flies expressing GFP(S65T) under the control of the distal actin *5c promoter (http://www-ibmc.u-strasb-g.fr/upr9022/GreenBalancers.html)* are used. two different microscopes are used, which provides images of similar quality. One is the Heidelberg Retina Angiograph (Heidelberg Engineering, Carlsbad, Calif.), a confocal laser-scanning system developed for digital fluorescein angiography in ophthalnic patients (Bartsch D U, et al., Confocal scanning infrared laser ophthalmoscopy for indocyanine green angiography. *American Journal of Ophthalmology*. 1995; 120:642–651). The other is a BIORAD MRC-1024 confocal microscope. Flies are anesthetized with a 50% solution of triethylamine and the wings are attached to glass slides. Images are recorded in digital form and analyzed with image analysis software (NIH Image). Absolute quantification of ventricular dimensions is obtained on these flies using the Nikon Diaphot-TMD microscope to scale the relative measurements obtained.

Example 2

Statistical Analysis

All results are expressed as mean ± standard error of the mean. Analysis of variance is used to analyze age-associated changes in heart rate with the Bonferroni correction for multiple comparisons. The incidence of fibrillation-like rhythm is analyzed using the Chi-square statistic.

The other comparisons are made using the t test. Values of $p<0.05$ are considered statistically significant.

Example 3

The Effects of Anesthesia on Heart Rate

This example establishes the effects of anesthesia on heart rate. $CO_2$ the most commonly employed anesthetic for *Drosophila*. This form of anesthesia was shown to cause cardiac arrest within a few seconds in *Drosophila* (n=10), with resumption of heart beat 20–30 seconds after cessation of gas exposure. Ethyl-ether was also shown to depress heart rate in flies. Heart rate was 120±19 beats per minute immediately after ether anesthesia but it increased to 248±11 beats per minute in the same flies after 30–40 min. when leg movements began to return (n=5, p=0.001). In contrast, triethylamine (TEA) was found to not cause significant changes in heart rate under the same conditions, either in young (10 days, 283±6 beats per minute vs. 282±4 beats per minute, n=6) or in older flies (48 days, 213±6 beats per minute vs. 211±11 beats per minute, n=7). Therefore, TEA was used for all subsequent experiments.

Example 4

Resting Heart Rate Declines with Age in *Drosophila*

Figure 1:
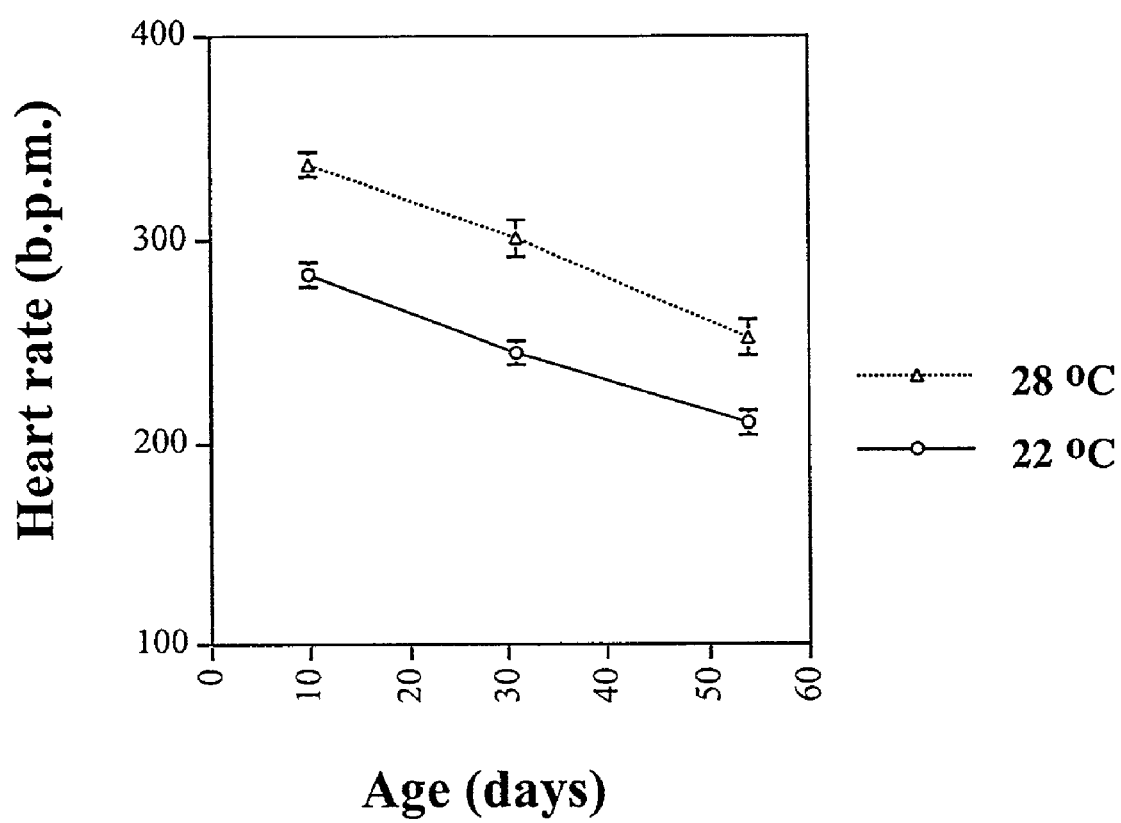
FIG. 1 depicts decline of heart rate (in beats per minute) with age both at 22° C. and at 28° C. The flies were studied at the ages of 10, 31 and 54 days. Heart rate was measured using the Diaphot microscope. Data are mean ± standard error of the mean.
Figure 2:
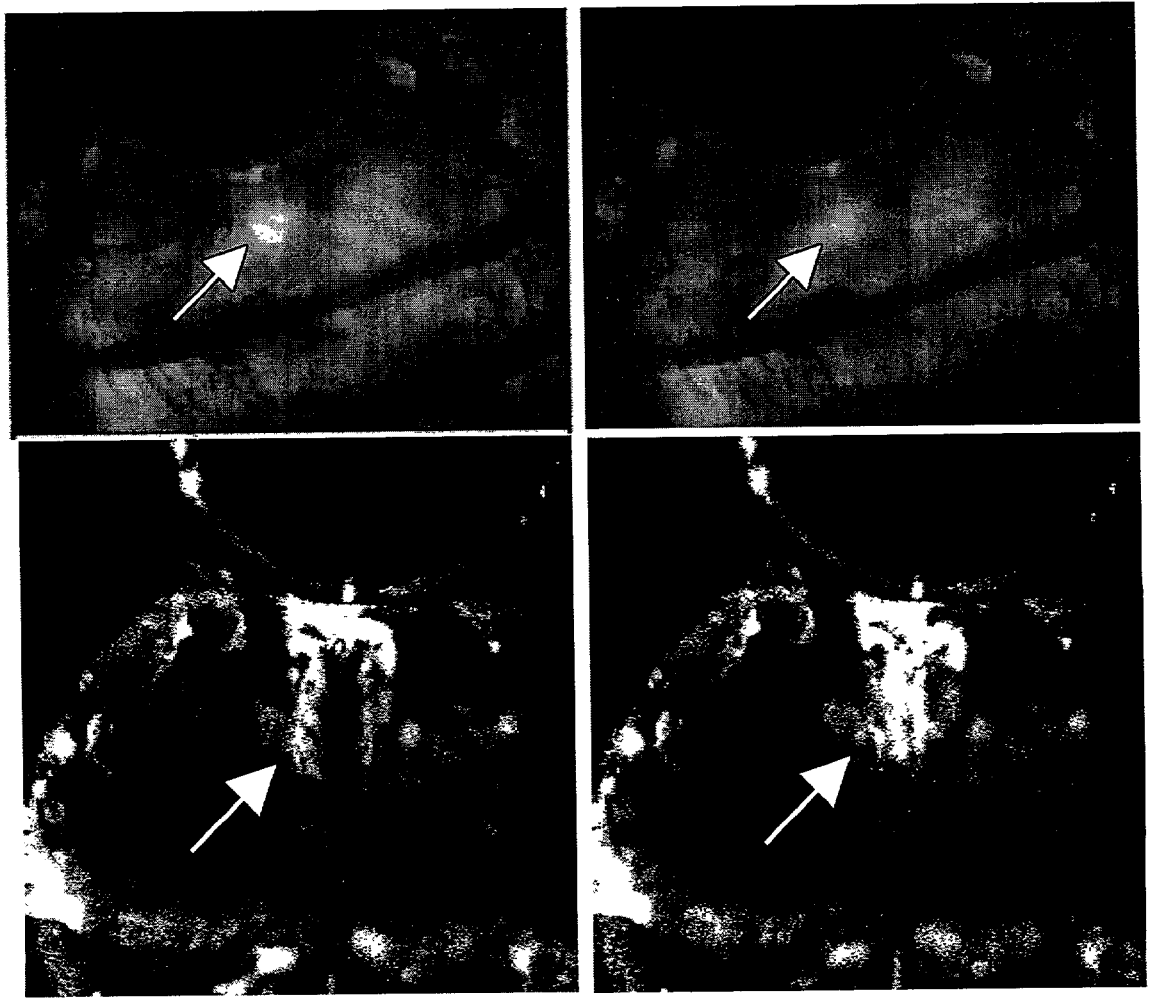
FIG. 2 depicts *Drosophila* heart. The images in the upper panels were obtained with the Nikon Diaphot microscope. The first ventricle of the heart is indicated by the arrow (left panel diastole, right panel systole), no marker (i.e. Green Fluorescent Protein) was used. The images in the lower panels were obtained using the BIORAD MRC-1024 confocal microscope in transgenic flies expressing S65T GFP under the control of the distal actin Sc promoter. A similar portion of the fly body as that in the upper panels is depicted. The left panel shows the *Drosophila* heart in diastole and right panel shows it in systole (the arrow points to the first ventricle).

This example establishes that resting heart rate declines with age in *Drosophila*. Average heart rate measured at room temperature (22° C.) decreased progressively with age (FIG. 1, Table 1). In male flies at 10 days of age, mean heart rate was 286±3 beats per minute (n=59), compared to 249±5 beats per minute (n=29) at 31 days and 220±3 beats per minute (n=64) at 54 days of age (p<0.01 for comparisons between all age-groups). A similar decrease in heart rate was also observed in female flies: 271±6 beats per minute at 10 days (n=14) vs. 189±5 beats per minute at 54 days (n=26) (p<0.01). The age-related decline in heart rate was also confirmed in the GFP transgenic strain: 275+8 beats per minute in 15-day-old flies versus 216±6 beats per minute in 56-day-old flies (p<0.01), measured at 22° C. An example of the images used for measuring heart rate is shown in FIG. 2.

TABLE 1

Heart rate at 22° C. and 28° C.

| Temp. | Age | Mean | SE | Median | 95% CI | n |
|---|---|---|---|---|---|---|
| 22 | 10 | 286 | 3 | 286 | 281–292 | 59 |
| 22 | 31 | 249 | 5 | 242 | 239–259 | 29 |
| 22 | 54 | 220 | 3 | 220 | 214–226 | 64 |
| 28 | 10 | 339 | 6 | 341 | 328–350 | 26 |
| 28 | 31 | 301 | 9 | 297 | 281–321 | 19 |
| 28 | 54 | 254 | 10 | 264 | 233–276 | 14 |

Table 1 summarizes the heart rate experiments performed in male flies at room temperature and at 28° C. Temperature in ° C.; age in days; mean, standard error of the mean, median and 95% confidence interval of the heart rate in beats per minute; n= number of animals.

Example 5

Temperature Stress-Tests Reveal Age-Associated Cardiac Impairment in *Drosophila*

This example establishes that temperature stress-tests reveal age-associated cardiac impairment in *Drosophila*. Using temperature stress-tests, where heart rates were measured at 28° C. a more pronounced effect of age on average heart rate was observed compared with measurements at 22° C. For every age group examined, increased ambient temperature resulted IN a faster heart rate. Average heart rate measured in male flies was 339±6 beats per minute (n=26) at 10 days of age, compared with 301±9 beats per minute at 31 days (n=19) and 254±10 bets per minute (n=14) at 54 days (FIG. 1, Table 1). The effects of age and temperature on mean heart rate were statistically significant for all pair-wise comparisons of the data (p<0.01).

Figure 3:
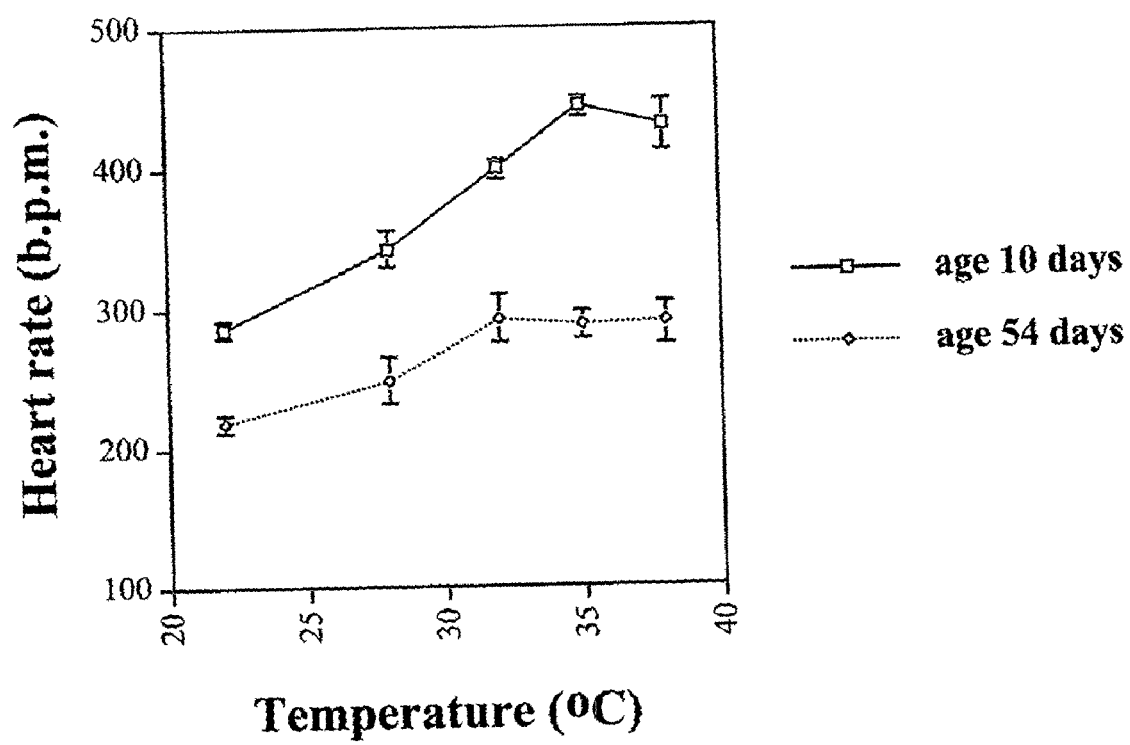
FIG. 3 depicts maximal heart rate during temperature stress in young and old flies. Heart rate (in beats per minute)

Using temperature stress tests, we studied flies at 28, 32, 35 and 38° C. (FIG. 3). For every age-group examined, temperature-induced increases in heart rate reached a plateau by 35° C. Using 35° C., therefore, for comparisons, we observed a decline in mean heart rate of flies with increasing age, from 440±7 beats per minute (n=10) at 10 days to 372±8 beats per minute (n=6) at 30 days to 288±10 beats per minute (n=9) at 54 days of age (p<0.01 between all groups) (FIG. 3).

Example 6

External Electrical Pacing of the Heart

External electrical pacing was used to estimate the maximal heart rate achievable in young and old flies. Electrical pulse interval could be decreased to a limit, beyond which heart rate failed to increase further. The maximum frequency of stimulated contractions was recorded as the estimated maximum achievable heart rate. Using this method, we found that maximum achievable heart rate is substantially lower in older flies: 411±13 beats per minute (n=15) in 10-day-old flies versus 303±8 beats per minute (n=14) in 59-day-old flies (p=0.0001) (FIG. 4).

Electrical pacing often triggered a fibrillation-like rhythm. The heart walls initially displayed very fine and fast tremors rather then full contractions and the heart subsequently stopped completely. Interestingly, fibrillation occurred in only 20% of 10-day-old flies (3/15) compared with almost 70% of 59-day-old flies (12/18) (p=0.02). Furthermore all younger flies tested (n=15) returned to normal rhythm within 2 minutes, whereas 40% of older flies that went into this fibrillation-like rhythm never recovered (5/18). These findings suggest the presence of age-associated electrophysiological defects in the hearts of aged flies.

Example 7

Heart Rate Variability

This example establishes heart rate variability. Using automated heart rate detection software, heart rate variability (that is oscillations in heart rate with time in each fly) between young (6-day-old, n=9) and aged flies (47-day-old, n=8) was compared. The coefficient of variation of heart rate was significantly larger in older animals: 14.8±1.4 (aged) vs. 9.2±0.4 (young) (p=0.001). We also confirmed with the automated image processing method the age-associated decline in heart rate (at 25° C.): 310±6 beats per minute (young) vs. 245±9 beats per minute (aged) (p<0.01), thus corroborating our results reported above.

Example 8

Estimation of End-Systolic and End-Diastolic Heart Dimensions

This example establishes the estimation of end-systolic and end-diastolic heart dimensions. Several methods were used to estimate end-systolic and end-diastolic dimensions, but failed to detect significant alterations associated with aging (at least within the resolution of our methods). For example, when using the same microscope utilized for heart rate determinations where images were recorded and film-frames were frozen at the end of systole or diastole, mean end-systolic diameters if 4.4±0.5 μm versus 4.0±0.7 μm and mean end-diastolic diameters of 34.8±1.15 μm (n=51) versus 36.8±1.15 μm (n=58) in 10-day-old compared to 54-day-old male flies were measured, respectively. The fractional shortening did not differ between the older (0.9±0.03) and the younger (0.87±0.01) flies.

Measurements of end-systolic and end-diastolic diameter of the fly heart were greatly assisted by imaging GFP-expressing transgenic flies. However, even in this case, no significant age-associated differences in cardiac dimensions were detected using two different microscopy techniques: end-systole 8.0±1 μm versus 7.5±1 μm and end-diastole 33±3 μm (n=18) versus 36±2 μm (n=14) in 10 day-old compared to 54 day-old flies, respectively. FIG. 2 shows an example of systolic and diastolic images in a fly.

Example 9

Identification of Genes Involved in Age-Related Cardiac Function

In order to identify genes involved in age-related cardiac dysfunction, a library of mutant strains of *Drosophila melanogaster* and a control non-mutant strain are obtained. The flies are studied under standard conditions and fed a standard diet. Similar groups of 6-day old mutant and normal flies are studied at a series of temperatures, ranging from 20° C. to 28° C., using methods disclosed herein. For example, groups of 40 flies expressing mutant gene "X" are studied at 20° C., 24° C. and 28° C. Groups of 40 flies expressing mutant gene "A" are also studied at 20° C., 24° C. and 28° C. In addition, control groups of 40 non-mutant flies are studied at 20° C., 24° C. and 28° C. Data is collected from 10 flies in each group. Each fly tested is anesthetized with a 50% solution of Flynap™, gently fixed to a slide and placed under a microscope, so that the heart of the fly can be imaged. The movements of the heart of the fly examined are digitally captured using a video camera. The resulting digital images are then analyzed with image-analysis software, such as NIH Image, and the data is tabulated.

Then the experiment is repeated with groups of 54-day old mutant "X", mutant "A" and normal flies, studied in the same manner as the groups of 6-day old flies. For example, 40 flies of each group are studied at 20° C., 24° C. and 28° C. Data are collected from 10 flies in each group of 54-day old flies. Data are collected from each 54-day old fly as is done with the 6-day old flies.

The data collected from the analysis of the digital images are compiled and analyzed, and the different groups of flies are compared. It is found that gene "X" has no effect on heart function, regardless of fly age or temperature. However, it is found that 54-day old gene "A" flies studied at 53° C. have dramatically worse heart function when compared with all other non-mutant control groups. Therefore, gene A is a candidate gene involved in age-related changes in cardiac function in *Drosophila* and its human homologues are candidate genes involved in age-related changes in cardiac function in humans.

Example 10

Identification of Genes Involved in Age-Related Cardiac Function

In order to identify genes involved in age-related cardiac function, normal *Drosophila melanogaster* are obtained. The flies are exposed to a mutagen and then maintained individually under standard conditions and fed a standard diet, at a series of temperatures, ranging from 20° C. to 28° C. For example, groups of 40 flies are studied at 20° C., 24° C. and 28° C. In addition, control groups of 40 non-mutagen-exposed flies are studied at 20° C., 24° C. and 28° C. Ten flies from each group are each examined at 6-days old, 27-days old and 54-days old. Each fly tested is anesthetized with a 50% solution of Flynap™, gently fixed to a slide and placed under a microscope, so that the heart of the fly can be imaged. The movements of the heart of the fly examined are digitally captured using a video camera. The resulting digital images are then analyzed with image-analysis software, such as NIH Image, and the data are tabulated.

The data collected from the analyses of the digital images are compiled and analyzed, and the different groups of flies are compared. It is found that most flies exhibited reductions in heart function over time, regardless of age or temperature. However, it is found that two flies exposed to the mutagen did not exhibit changes in cardiac function with increasing age. These flies are used to clone the genes affected by exposure to the mutagen, which prevented age-associated changes in cardiac function, by standard breeding and cloning techniques and classical techniques of linkage and recombinational analysis.

Example 11

Identification of Agents Affecting Age-Related Cardiac Function

In order to identify agents affecting age-related cardiac function, a library of compounds is obtained. *Drosophila melanogaster* with normal heart function and mutants with abnormal heart function are also obtained. The flies are maintained under standard conditions and fed a standard diet. Groups of 40 flies are studied at a series of temperatures, ranging from 20° C. to 28° C. For example, 20° C., 24° C. and 28° C. The flies are fed compound "X" during all their adult lifespan. Data are collected from 10 54-day old flies in each group. Each fly tested is anesthetized with a 50% solution of Flynap™, gently fixed to a slide and placed under a microscope, so that the heart of the fly can be imaged. The movements of the heart of the fly examined are digitally captured using a video camera. The resulting digital images are then analyzed with image-analysis software, such as NIH Image, and the data are tabulated.

Then the experiment is repeated with control flies, such as wild type flies, not fed any compound and groups of flies fed compounds consisting of the group compound "Y," compound "Z." compound "A," compound "B." and compound "C".

The data collected from the analysis of the digital images are compiled and analyzed, and the different groups of flies are compared. It is found that 54-day old flies studied at 24° C. and fed compound "A" have dramatically improved heart function when compared with all other test groups. All other test compounds have no effect on heart function when fed to any group of flies examined. Therefore, compound A is a candidate agent able to affect age-related changes in cardiac function.

REFERENCES

All publications, including patent documents and scientific articles, referred to in this application and the bibliography are incorporated by reference herein in their entirety for all purposes to the same extent as if each individual publication is individually incorporated by reference.

Paternostro G, et al. Age-associated cardiac dysfunction in *Drosophila melanogaster, Circulation Research,* 2001; 88:1053–1058.

Adams M D, et al. The genome sequence of *Drosophila melanogaster. Science.* 2000;287:2185–2195.

Rizki T M. The Circulatory System and Associated Cells and Tissues. In: Ashburner M, Wright TRF, Eds. *The Genetics and Biology of Drosophila.* London: Academic Press; 1978:397–452.

Bodmer R, Venkatesh T V. Heart development in *Drosophila* and vertebrates: conservation of molecular mechanisms. *Developmental Genetics.* 1998;22:181–186.

Lints T J, et al. Nkx-2.5: a novel murine homeobox gene expressed in early heart progenitor cells and their myogenic descendants. *Development.* 1993;119:419–431.

Komuro I, Izumo S. Csx: a murine homeobox-containing gene specifically expressed in the developing heart. *Proceedings of the National Academy of Sciences of the United States of America.* 1993;90:8145–8149.

Curran M E, et al. A molecular basis for cardiac arrhythmia: HERG mutations cause long QT syndrome. *Cell.* 1995; 80:795–803.

Warmke J W, Ganetzky B. A family of potassium channel genes related to eag in *Drosophila* and mammals. *Proc Natl Acad Sci USA*. 1994;91:3438–3442.

Min K T, Benzer S. Preventing neurodegeneration in the *Drosophila* mutant bubblegum. *Science*. 1999;284:1985–1988.

Kazemi-Esfanari P, Benzer S. Genetic suppression of polyglutamine toxicity in *Drosophila*. *Science*. 2000;287:1837–1840.

Feany M B, Bender W W. A *Drosophila* model of Parkinson's disease. *Nature*. 2000;404:394–398.

Rose M R. *Evolutionary Biology of Aging*. New York: Oxford University Press; 1991.

Lin Y J, Seroude L, Benzer S. Extended life-span and stress resistance in the *Drosophila* mutant methuselah. *Science*. 1998;282:943–946.

American Heart Association. 2000 *Heart and Stroke Statistical Update*. Dallas, Tex.: American Heart Association; 1999.

Fleg J L, et al. Inpact of age on the cardiovascular response to dynamic upright exercise in healthy men and women. *Journal of Applied Physiology*. 1995;78:890–900.

Lakatta E G. Circulatory function in younger and older humans in health. In: Hazzard W R, Blass J P, Ettinger W H, Halter J B, Ouslander J G, eds. *Principles of geriatric medicine and gerontology*. New York: McGraw-Hill; 1999:645–660.

Rich M W. Heart failure. In: Hazzard W R, Blass J P, Ettinger W H, Halter J B, Ouslander J G, eds. *Principles of geriatric medicine and gerontology*. New York: McGraw-Hill; 1999:679–700.

Bartsch D U, et al. Confocal scanning infrared laser ophthalmoscopy for indocyanine green angiography. *American Journal of Ophthalmology*. 1995;120:642–651.

Chatfield C. *The Analysis of Time Series*. London: Chapman and Hall; 1980.

Armitage P, Berry G. *Statistical methods in medical research*. 3rd ed. Oxford: Blackwell Scientific; 1994.

Burch G E, Sohal R S, Fairbanks L D. Senescent changes in the heart of *Drosophila* repleta Wollaston. *Nature*. 1970; 225:286–288.

Burch G E, et al. Ultrastructural changes in *Drosophila* heart with age. *Archives of Pathology & Laboratory Medicine*. 1970;89:128–136.

Le Bourg E, Lints F A. Hypergravity and aging in *Drosophila melanogaster*. 4. Climbing activity. *Gerontology*. 1992;38:59–64.

Ganetzky B, Flanagan J R. On the relationship between senescence and age-related changes in two wild-type strains of *Drosophila melanogaster*. *Experimental Gerontology*. 1978;13:189–196.

Jose A D. Effect of combined sympathetic and parasympathetic blockade on heart rate and cardiac function in man. *American Journal of Cardiology*. 1966;18:476–478.

Roberts J, Goldberg P B. Changes in basic cardiovascular activities during the lifetime of the rat. *Experimental Aging Research*. 1976;2:487–517.

Yu B P, et al. Life span study of SPF Fischer 344 male rats fed ad libitum or restricted diets: longevity, growth, lean body mass and disease. *Journal of Gerontology*. 1982;37: 130–141.

Sinclair D A, Mills K, Guarente L. Molecular mechanisms of yeast aging. *Trends in Biochemical Sciences*. 1998;23: 131–134.

Pennisi E. Evolutionary trends from bacteria to birds. *Science*. 2000;289:1131–1133.

Tower J. Aging mechanisms in fruit flies. *BioEssays*. 1996; 18:799–807.

Ohno S. Ancient linkage groups and frozen accidents. *Nature*. 1973;244:259–262.

Fortini M E, et al. A survey of human disease gene counterparts in the *Drosophila* genome. *Journal of Cell Biology*. 2000;150:F23–F30.

Lakatta E G. Heart aging: A fly in the ointment? *Circulation Research* 2001; 88:984–986.

Nusslein-Volhard, C., and Wieschaus, E. 1980. Mutations affecting segment number and polarity in *Drosophila*. *Nature* 287:795–801.

White, K., Grether, M. E., Abrams, J. M., Young, L., Farrell, K., and Steller, H. 1994. Genetic control of programmed cell death in *Drosophila*. *Science* 264:677–683.

Artavanis-Tsakonas, S., Muskavitch, M. A., and Yedvobnick, B. 1983. Molecular cloning of Notch, a locus affecting neurogenesis in *Drosophila melanogaster*. *Proc Natl Acad Sci USA* 80:1977–1981.

White, L. A., Ringo, J. M. and Dowse H. B. Effects of deuterium oxide and temperature on heart rate in *Drosophila melanogaster* 1992. *J Comp Physiol B* 162:278–83.

Johnson, E., Ringo J. and Dowse H. Modulation of *Drosophila* heartbeat by neurotrasmitters. 1997. *J Comp Physiol B* 167:89–97.

Nichols R., Kaminski, S. Walling, E., Zomik, E., Regulating the activity of a cardioacceleratory peptide. 1999. *Peptides* 20:1153–58.

Braunwald, E, 2001. *Heart Disease*, W B Saunders, Philadelphia.

Ashburner M, 1989. *Drosophila. A Laboratory Manual*, Cold Spring Harbor Laboratory Press, Cold Spring Harbor.

Lacey A J, 1999. *Light Microscopy in Biology*, Oxford University Press, Oxford.

Inoue S and Spring K R, 1997. *Video Microscopy: The Fundamentals*, Plenum Press, New York.

Baldock R and Granam J, 2000. *Image Process Analysis*, Oxford University Press, Oxford.

Roberts D B, 1998. *Drosophila*, Oxford University Press, Oxford.

What is claimed is:

1. A method of screening for a gene affecting the cardiac function comprising the steps of:
   a. providing an adult *Drosophila*;
   b. imaging the heart of said *Drosophila*;
   c. measuring the movements of the heart in the image; and
   d. analyzing the measurements of the movements;
whereby the analysis of said measurements are indicative of the cardiac function of said *Drosophila* and changes in the function are indicative of the effect of said gene on the cardiac function of said *Drosophila*.

2. The method of claim 1 further including the step of electrically pacing the heart with electrodes and a pulse generator, so that parameters selected from the group consisting of the maximal heart rate and the frequency of occurrence of fibrillation-like rhythm are determined.

3. The method of claim 1 further including the step of increasing the temperature to stress the heart.

4. The method of claim 1 wherein the effect of said gene on age-related changes in said cardiac function is determined.

5. The method of claim 1 wherein said *Drosophila* is a *Drosophila melanogaster*.

6. The method of claim 1, wherein said *Drosophila* is anesthetized.

7. The method of claim 6, wherein the anesthesia is caused by triethylamine.

8. The method of claim 1, wherein said *Drosophila* is positioned under a microscope so that the light beam of said microscope is generally perpendicular to the frontal plane of said *Drosophila* and is directed on the heart of said *Drosophila* and produces said image.

9. The method of claim 8, wherein contrast enhancement means are combined with said microscope to improve said image of said heart.

10. The method of claim 8 wherein said microscope is a fluorescence microscope and said *Drosophila* expresses a fluorescent protein in the heart.

11. The method of claim 10, wherein said fluorescent protein is green fluorescent protein.

12. The method of claim 1, wherein the movements of the walls of said heart are measured.

13. The method of claim 12 wherein said measure of the movements of said heart walls is heart rate.

14. The method of claim 1, wherein the measurements are compared to a control set of data.

15. The method of claim 1, wherein said genes is mutated.

16. The method of claim 15, wherein said mutation causes a change in expression of said gene.

17. The method of claim 16, wherein the change in expression of said gene causes age-related changes in said cardiac function.

18. The method of claim 15, wherein said mutation causes age-related changes in cardiac function.

19. A method of screening for agents affecting cardiac function comprising the steps of:
   a. providing an adult *Drosophila;*
   b. exposing said *Drosophila* to an agent:
   c. imaging the heart of said *Drosophila;*
   d. measuring the movements of the heart in the image; and
   e. analyzing the measurements of the movements;
whereby the analysis of said measurements are indicative of the cardiac function of said *Drosophila* and changes in the function are indicative of the effect of said agent on the cardiac function of said *Drosophila*.

20. The method of claim 19 further including the step of electrically pacing the heart with electrodes and a pulse generator, so that parameters selected from the group consisting of the maximal heart rate and the frequency of occurrence of fibrillation-like rhythm are determined.

21. The method of claim 19 further including the step of increasing the temperature to stress the heart.

22. The method of claim 19 wherein the effect of said agent on age-related changes in the cardiac function is determined.

23. The method of claim 19, wherein the measurements are compared to a control set of data.

24. The method of claim 19, wherein said *Drosophila* is a *Drosophila melanogaster*.

25. The method of claim 19, wherein said *Drosophila* is anesthetized.

26. The method of claim 25, wherein the anesthesia is caused by triethylamine.

27. The method of claim 19, wherein said *Drosophila* is positioned under a microscope so that the light beam of said microscope is about perpendicular to the frontal plane of said *Drosophila* and is directed on the heart of said *Drosophila* and produces said image.

28. The method of claim 27, wherein contrast enhancement means are combined with said microscope to improve the image of the heart.

29. The method of claim 27 wherein said microscope is a fluorescence microscope and said *Drosophila* expresses a fluorescent protein in the heart.

30. The method of claim 29, wherein said fluorescent protein is green fluorescent protein.

31. The method of claim 19, wherein the movements of the walls of said heart are measured.

32. The method of claim 31 wherein said measure of the movements of said heart walls is heart rate.

33. The method of claim 19, wherein the measurements are compared to a control set of data.

* * * * *